United States Patent [19]

Krensky et al.

[11] Patent Number: 4,994,369

[45] Date of Patent: Feb. 19, 1991

[54] T-CELL ACTIVATION RELATED GENE

[75] Inventors: Alan M. Krensky, Stanford; Mark Davis, Mountain View; Thomas Schall, Palo Alto, all of Calif.; Jan Jongstra, Toronto, Canada

[73] Assignee: The Board of Trustees of the Leland Stanford Jr. Univ., Stanford, Calif.

[21] Appl. No.: 132,926

[22] Filed: Dec. 15, 1987

[51] Int. Cl.[5] .......................... C12Q 1/68; C12Q 1/00
[52] U.S. Cl. ........................................ 435/6; 435/7.24
[58] Field of Search ........................................ 435/6, 7

[56] References Cited

PUBLICATIONS

Sakaguchi et al., (1986) Embo J., 5:2139–2147.
Kronke, et al., "Sequential Expression of Genes Involved in Human T Lymphocyte Growth and Differentiation" in *J. Exp. Med.* (1985) 161:1593–1598.
Miyamoto, et al., "Regulated Expression of a Gene Encoding a Nuclear Factor, IRF-1, That Specifically Binds to IFN-β Gene Regulatory Elements" in *Cell* (1988) 54:903–913.
Landschult, et al., "The leucine Zipper: A Hypothetical Structure Common to a class of DNA binding Proteins" in *Science* 240:1759–1764.
Mazrimas, et al., "A Corrected Primary Sequence for Bull Protamine" in *Biochem. Biophys. Acta.* (1986) 872:11–15.
O'Brien, et al., "Coding of Two Sphingolipid Activator Proteins (SAP-1 and SAP-2), by the Same Genetic Locus" in *Science* (1988) 241:1098–1101.
Jongstra, et al., "The Isolation and Sequence of a Novel Gene From a Human Functional T Cell Line" in *J. Exp. Med.*, (1987) 165:601–614.

*Primary Examiner*—Robin L. Teskin
*Assistant Examiner*—Beth A. Burrous
*Attorney, Agent, or Firm*—Bertram I. Rowland

[57] ABSTRACT

Nucleic acids and peptides are provided which can be used for detecting the status of functional T-lymphocytes as to stimulation and the time of stimulation. The nucleic acids and peptides may be provided by cloning and expression using recombinant techniques. These diagnoses may be used to determine whether T-cells are functional and the degree to which a T-cell population has been stimulated.

1 Claim, No Drawings

T-CELL ACTIVATION RELATED GENE

INTRODUCTION

Technical Field

Novel amino acid and nucleic acid sequences are provided associated with activated T-cells. The compositions find use in diagnosing activated T-cells, as markers, and modifying T-cell response.

Background

The immune system has proven to be an extraordinarily subtle intricate system involving manifold cell types, cellular interactions, and chemical messengers. The importance of the immune system to the well-being of mammalian hosts requires that continued efforts be made to understand the immune system and to develop methods whereby the immune system may be regulated to a specific or general purpose. Essential to the immune system is the ability of the immune system to activate cells specifically associated with a stimulus, so that the major cell population remains unstimulated, while only those cells of the immune system required to respond to the stimulus are activated and proliferate. The manner in which this specificity occurs, the mechanism by which it is up- or down-regulated, and the materials involved in this regulation are of substantial importance.

One component of the immune system is the T-cell, whose role appears to be central to the operation and regulation of the immune system. The T-cell is involved in stimulating B-cells to proliferate, in cytotoxic activity, and in suppressing immune response. In order to understand the role of the T-cell, it is necessary to understand the cellular biological pathways involved in the immune response. It is therefore of importance to be able to determine whether the system is functioning and how to modify the system to control the immune response. Towards this end, specific genes and proteins must be identified so as to determine their role in the immune response.

RELEVANT LITERATURE

The genes associated with stimulation of T-cells, some of which code for molecules related to the development of effector function include: for IL-2 (interleukin-2) Smith, *Ann. Rev. Immunol.* (1984) 2:319; Thireos et al., *Proc. Natl. Acad. Sci. USA* (1984) 81:5096; and Fujita et al., *Cell* (1986) 46:401; IL-2 receptor (Kroenke et al., *J. Exp. Med.* (1985) 161:1593 and Greene and Leonard, *Ann. Rev. Immunol.* (1986) 4:69); and serine proteases (Gershenfeld and Weissman, *Science* (1986) 232:854, Love et al., *Science* (1986) 232:858; Brunet et al., *Nature* (1986) 322:268). Inducible expression of the proto-oncogene c-myc and other genes of unknown function have been reported by Kroenke et al., supra and Brunet et al., supra. Cell surface proteins associated with stimulation have also been reported (Krensky and Clayberger, Transplantation (1985) 39:339, Suciu-Foca et al. *Nature* (1986) 318:465, and Hemler, *J. Immunol.* (1984) 1332:3011). Jongstra et al., *J. Exp. Med.* (1987) 165:601–614, report the results contained herein.

SUMMARY OF THE INVENTION

Nucleic acid sequences and peptides are provided for detecting functional activated T-cell lymphocytes, distinguishing between neoplastic and non-neoplastic tumor cells, and for use in modulating normal T-cell activity. In particular, messenger RNA has been isolated and sequenced which has been shown to be associated with stimulated T-cells and not with other types of cells, including cell tumor lines.

DESCRIPTION OF THE SPECIFIC EMBODIMENTS

Nucleic acid sequences and peptides are provided which are associated with stimulated functional human T-cells, where the absence of messenger RNA is diagnostic of cells other than stimulated T-cells. Therefore, evidence of the presence of the designated messenger RNA, or the protein expressed from the designated messenger RNA, is indicative of a stimulated T-cell which is not a tumor. In this manner, one can readily distinguish between a functional stimulated T-cell which is normal, a T-cell tumor, or a normal non-stimulated T-cell.

As exemplary of genes that are expressed in functional stimulated T-cells and not in other cells or T-cell tumors, is the gene which will be designated 519. This gene may be characterized as being expressed in IL-2 dependent and antigen driven T-cells or T-cells activated with a mitogen. The expression of 519 is stimulated with antigen in a mixed lymphocyte reaction or with a mitogen, such as phytohemagglutinin, generally being induced at least 10-fold. Upon stimulation, a relatively low level of 519 is induced, but in excess of about 90 hours, usually in excess of about 100 hours and less than about 150 hours, a substantial increase in the expression of 519 occurs where the level remains reasonably constant for at least about 50 hours.

The gene appears to be of at least one and not greater than about two copies in the host cell. The messenger RNA, excluding the polyA tail, is equal to or greater than about 853 nucleotides (nt).

The protein has a molecular weight ($M_r$) of about 15,000 and an amino acid sequence of about 129 amino acids. The amino acid sequence as deduced from the nucleic acid sequence as depicted in conjunction with the nucleic acid sequence of the 519 messenger RNA. The peptide may be provided in substantially pure form, generally of at least about 90% purity, usually greater than about 99% purity.

The nucleic acid sequence is associated with a functional T-cell and not other types of cells, and can be isolated by construction of a cDNA library employing a functional T-cell line, e.g. a cytolytic or helper T-cell line. The desired cDNA sequences may then be enriched by hybridizing for a $C_ot$ of greater than about 2,000 mol.sec/liter with other than a stimulated functional T-cell line, particularly a B-cell line. The unhybridized resulting enriched cDNA fraction may then be cloned and screened with a second enriched radioactive cDNA preparation from an activated T-cell line. Screenings may be repeated until a limited number of positive clones are obtained. The number of positive clones may be further reduced by subtracting for rare abundance messenger RNAs.

Clones having inserts of at least about 300 base pairs may then be selected and used for Northern blots to identify messenger RNA in a variety of cells. To ensure for a complete coding sequence, the positive clones may be sequenced, where one or more of the clones, by themselves or in combination where overlapping, are shown to provide a complete coding sequence. The open reading frame(s) may then be identified.

Employing the cDNA as a probe, genomic libraries may be screened for the genomic sequence. In this manner, the gene containing any introns may be isolated and used in place of the cDNA. In addition, the 5'-non-coding region may be isolated and sequenced so as to provide for an inducible transcription initiation region which can be used in T-cells or in other cells for induction by mitogens or lymphokines.

Once the cDNA has been established as providing the complete coding sequence, the cDNA or the coding portion thereof, it may be used for expression of the protein. Various expression vectors are commercially available or have been described in the literature or, alternatively, may be prepared. The cDNA encoding the protein may be inserted downstream from an appropriate transcriptional and translational initiation region which is functional in an expression host. Downstream from the cDNA gene will be a functional transcriptional and translational termination region allowing for termination of the messenger and termination of translation. The expression cassette comprising in the direction of transcription, a transcriptional and translational initiation region, the open reading frame with initiation and stop codons and a translational and transcriptional termination region, may be part of a vector capable of stable extrachromosomal maintenance in an appropriate cellular host or may have cDNA homologous with the chromosome of the host for insertion. Alternatively, the expression cassette may be bordered by sequences which allow for insertion into a host, such as transposon sequences, lysogenic viral sequences, or the like. Desirably, markers are provided with the expression cassette, which allow for selection of host cells containing the expression cassette. The marker may be on the same or a different DNA molecule, desirably the same DNA molecule.

The DNA may be introduced into the host by any convenient means, including fusion, conjugation, transfection, transduction, electroporation, injection, or other convenient means. Selection of host cells containing the expression cassette may then be selected for by means of the marker. Convenient markers include resistance to a cytotoxic agent, complementation of an auxotrophic host to prototrophy, production of a detectable product, etc.

The transformed cells may be screened and positive clones expanded and used for expression of the peptide. Expression cassettes can be provided which allow for secretion of the peptide by joining the peptide in reading frame with a signal sequence and processing signal which allows for secretion of the peptide and cleavage of the signal sequence at the processing site from the peptide. These techniques may be found in a wide number of patents, patent applications, and scientific articles. See for example, U.S. Pat. Nos. 4,599,308, 4,601,980, 4,612,287 and 4,615,974.

A wide variety of hosts may be employed for expression of the peptides, both prokaryotic and eukaryotic. Useful hosts include bacteria, such as E. coli, yeast, filamentous fungus, immortalized mammalian cells, such as various mouse lines, monkey lines, chinese hamster ovary lines, human lines, or the like. For the most part, the mammalian lines will be immortalized by transformation to a neoplastic state, where the cells may be isolated from a neoplastic host, or wild-type cells may be transformed with oncogenes, tumor causing viruses, or the like.

Depending on the presence of a secretory signal sequence, the peptide may be isolated from the supernatant in which the expression host is grown or from a lysate of the expression host. The peptide may then be isolated by conventional techniques employing HPLC, electrophoresis, gradient centrifugation, affinity chromatography, etc., to provide a substantially pure product, particularly free of human cell component contaminants. The peptide may be employed as crossreactive fragments in a variety of applications, where the fragment will have at least 8, usually about 12, amino acids.

The peptides of the subject invention may be used for producing antibodies, either polyclonal or monoclonal. The antibodies are produced by immunizing an appropriate vertebrate host, e.g. mouse, with the peptide, by itself or in conjunction with a conventional adjuvant. Usually, two or more immunizations will be involved and the blood or spleen will be harvested a few days after the last injection. For polyclonal antisera, the immunoglobulins may be precipitated, isolated and purified, including affinity purified. For monoclonal antibodies, the splenocytes normally will be fused with an immortalized lymphocyte, e.g. a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570 and 4,618,577.

All of the subject compositions may find use in diagnosis. Nucleic acid, either RNA or DNA, particularly DNA. may be used as a probe. Usually, the probe will have a specific complementary sequence of at least eight nucleotides, more usually at least about twelve nucleotides, and may have the entire coding region, the entire non-coding region, combinations thereof, or portions thereof. The probes may be modified by being conjugated to a wide variety of labels which allow for detection of the duplex. Labels include radioactive isotopes, ligands, e.g. biotin, enzymes, fluorescers, and the like. A variety of protocols for detecting duplexes have been described in the literature. See for example U.S. Pat. No. 4,302,204; Maniatis et al., *Molecular Cloning, A Laboratory Manual* (1982) CSH Laboratories, Cold Spring Harbor, NY.

The peptide and antibodies may be used in competitive or non-competitive assays for the detection of the peptide. A large number of immunoassays have been reported, where the antibody and/or the peptide may be labeled with a label capable of providing, either directly or indirectly, a detectable signal. A wide variety of labels have been reported in the literature, such as radioisotopes, enzymes, fluorescers, enzyme substrates, cofactors and inhibitors, particles, e.g. magnetic particles, carbon, etc., ligands, e.g. biotin, or the like. The assays may be competitive or non-competitive, heterogeneous or homogeneous. When neither the peptide nor the antibody is labeled, a second antibody may be used which is specific for the antibody and which is labeled. In this manner, the formation of an immune complex may be detected without any of the members of the complex being labeled. Illustrative of various protocols which may be employed with the subject compostions are U.S. Pat. Nos. 3,791,932, 3,850,752, 3,935,074 and 4,174,384.

The detection of transcription or expression of a peptide specific for a stimulated T-cell may find a variety of uses. In culture, it may be of interest to determine whether the cells are capable of antigenic or mitogenic stimulation. In a cell culture containing T-cells, it may be of interest to determine whether a deficiency in any particular peptide is inhibiting the stimulation of the T-cells. The absence of the formation of these particular peptides may be indicative of a neoplastic condition. In addition, by following the levels of particular peptides of a particular cell population, one can detect, to some degree, the period of time which transpired since the cell population was stimulated or if particular members of the cell population have been stimulated. This may be of great importance where cytopheresis is employed and a particular T-cell population is to be stimulated. By employing the subject assays, one could detect the effectiveness of the stimulation in producing the desired cellular proliferation. Other utilities for the subject compositions may also be available.

The following examples are offered by way of illustration and not by way of limitation.

EXPERIMENTAL METHODS

Cell Lines

The characterization and growth of the functional T-cell lines and clones has been described (Krensky et al., *Proc. Natl. Acad. Sci. USA* (1982a) 79:2365; Krensky et al., *J. Immunol.* (1982) 129:2001).

Construction of cDNA Libraries

Construction of a cDNA library enriched for T-cell specific sequences was as described (Davis et al., *Proc Natl. Acad. Sci. USA* (1984) 81:2194; Davis, "Subtractive cDNA hybridization and the T-cell receptor genes" in *Handbook of Experimental Immunology* (1986) 2:76.1 Blackwell Scientific Publications, Palo Alto, California) with minor modifications. Briefly, total cytoplasmic RNA was extracted from the CD8+, HLA-A2 specific functional human cytolytic T-cell line AH2 (Krensky et al., supra (1982a)) by NP-40 lysis. PolyA+ messenger RNA was prepared by oligo-dT chromatography (Aviv and Leder, *Proc. Natl. Acad. Sci. USA* (1972) 69:1408). Single stranded cDNA was synthesized using reverse transcriptase primed with oligo-dT$_{(12-18)}$ in the presence of actinomycin D. To enrich for cDNA sequences specific for functional T-cell lines, approximately 1 μg of total cDNA was then hybridized to a $C_ot$ of >2,000 mol.sec/l with 10 μg of oligo-dT selected messenger RNA extracted from the EBV transformed B-cell line LB. Approximately 100 ng of unhybridized cDNA was recovered with a yield of 65-70%. It is estimated that the unhybridized cDNA was enriched approximately sevenfold for T-cell specific sequences. This cDNA was made double stranded and C-tailed and annealed with G-tailed pUC9 (Pharmacia) as in Davis supra (1984, 1986), except that 10 μg of oligo-rA (Pharmacia) was used as a carrier. The annealed DNA was then used to transform competent *E. coli* HB101 (BRL). The final subtracted cDNA library consisted of 20,000 colonies.

To isolate (near) full-length cDNA clones of the genes identified in the subtracted library, a cDNA library was constructed using total cytoplasmic polyA+ RNA from the AH2 cell line. First and second strand synthesis of the cDNA was according to the method of Gubler and Hoffman, *Gene* (1983) 25:263. This double stranded cDNA was then cloned in the λ-phage gt10 (λgt10) using EcoRI linkers as described by Huynh et al., "Construction and screening cDNA lbraries in λgt10 and λgt11," in *DNA cloning: A Practical Approach* (1985) D. Glover ed., IRL Oxford. After in vitro packaging using a commercial packaging extract (Amersham) and plating on *E. coli* C600, $1.5 \times 10^7$ phage plaques were obtained. Approximately 2% of these plaques were due to recombinant phages capable of replicating in *E. coli* C600 Hfl+. Screening of the library was performed after plating $10^5$ recombinant phages on *E. coli* C600 Hfl+.

Screening With Subtracted cDNA Probes

Radioactive subtracted probes were prepared as described (Davis, supra, (1984, 1986)). Briefly, cDNA from AH2 cells labeled to high specific activity ($10^8$ cpm/μg) with $^{32}$P-dCTP was subtracted twice with RNA from LB cells. The final single stranded probe ($2 \times 10^7$ cpm) was used to screen four large nitrocellulose filters, each containing 5,000 colonies of the AH2-LB, T-B subtracted cDNA library. Hybridization was in 3.5 ml aqueous buffer containing 1M Na+ at 68° C. for 20 hours. Filters were washed twice in 2×SSC at 65° C. for 30 minutes.

Isolation of Cytoplasmic RNA

Cells ($10^9$) were spun down and washed once in ice-cold phosphate buffered saline (PBS). Cells were resuspended in 10ml ice-cold lysis buffer (0.14M NaCl, 0.01M Tris, pH 8.0, 1.5 mM MgCl$_2$) and 10 ml ice-cold lysis buffer containing 0.8% NP-40 was added. The cell suspension was placed on ice for two minutes before pelletting the nuclei at 800×g for 5 minutes. The supernatant was made 1% in SDS and 5mM in EDTA, and extracted twice with phenol at 65° C and once with chloroform. The aqueous phase was then made 0.3M in sodium acetate and the RNA was precipitated wth 2.2 volumes of ethanol at −20° C. overnight. The RNA precipitate was then pelletted at 2,500×g for 30 minutes. After drying the pellet, the RNA was resuspended in 0.1 ml H$_2$O.

Isolation of Whole Cellular RNA

This was done according to the guanidinium isothiocyanate method described by Chirgwin et al., *Biochemistry* (1979) 18:5294.

Northern Blot Analysis

RNA was separated on gels containing 1% agarose, 3% formaldehyde, 1 mM EDTA in 20 mM sodium borate buffer, pH 8.3. RNA samples were made 50% formamide, 6% formaldehyde, 2 mM EDTA and 10% glycerol in 20 mM sodium borate buffer, pH 8.3, and heated to 55° C. for 15 minutes prior to loading. Gels were run for 8 hours at 80 volts, and the RNA was transferred to Genetran nylon filters (Plasco, Woburn, MA) by blotting the gel overnight.

Hybridization of Northern Blots

Whole plasmids were labeled with $^{32}$P by nick translation. DNA fragments were labeled with Klenow enzyme using random hexamer priming (Feinberg and Vogelstein, *Anal. Biochem.* (1983) 132:6). The nylon filters were prehybridized for 4 hours at 42° C. and hybridized at the same temperature overnight with $3 \times 10^6$ cpm of probe per ml of hybridization buffer. Prehybridization and hybridization buffers were 3×SSC, 50% formamide, 1% SDS, 0.5 mM sodium pyrophosphate, 0.1M sodium phosphate, pH 7.0, 2.5×Denhardts solution, 100 μg/ml salmon sperm DNA and 2.4% dextran sulphate. Filters were washed twice for 20 minutes in 2×SSC, 0.1% SDS at room temperature, followed by a 30 minute wash in 0.2×SSC, 0.1% SDS at 60° C.

Sequence Analysis of cDNA Clones cDNA clones were sequenced using the method of Maxam and Gilbert. The sequence of the 5' end of clone 519.11 was verified using the chain termination method of Sanger et al., *Proc. Natl. Acad. Sci. USA* (1977) 74:5463. The DNA sequence of the two overlapping clones, AH2-519 and 519.11 (described subsequently) and the predicted protein sequence were compared against published sequences compiled in the GenBank and NBRF databases on a VAX 11/785 computer using the FASTP program (Lipman and Pearson, *Science* (1985) 227:1435.

The DNA sequence of 519 mRNA set forth below, therefore, is a composite of the DNA sequence of the two overlapping clones AH2-519 and 519.11. The predicted amino acid sequence of the 519 gene product is shown beneath the DNA sequence from nucleotide 281 to 668. The polyadenylation signal starting at nucleotide 825 is underlined.

In Vitro Transcription and Translation

After subcloning the cDNA insert of phage 519.11 into the EcoRI site of the plasmid vector pGem-1 (Promega Biotec), RNA was transcribed from both strands using either SP6 or T7 polymerase. The transcription reactions were performed in the presence of 500 μM diguanosine-triphosphate, G(5') ppp (5')G, and 50 μM dGTP (Krieg and Melton, *Nucl. Acids Res.* (1984) 12:7057). Reactions were terminated by digestion of the DNA template with RNAse-free DNAse I (RQ DNAse, Promega Biotec) and the RNA was purified by phenol and chloroform extractions, followed with G-50 chromatography and ethanol precipitation. RNA from both strands was then translated in vitro (0.3μg each) using a commercial rabbit reticulocyte extract (Promega Biotec) in the presence of $^{35}$S-methionine. The translation products were analyzed using a 20% polyacrylamide gel prepared and run according to Laemmli.

Genomic Southern Blot Analysis

Genomic DNA was digested with restriction enzymes in the presence of 4mM spermidine. The digested DNA samples were made 2.5% Ficoll, and 10 μg DNA was separated on a 0.7% agarose gel in TAE buffer for 20 hours at 40 volts. The DNA was transferred to nitrocellulose paper (Schleicher and Schuell, Keene, NH) by blotting, using 20×SSC for 24 hours. The filter was then baked at 80° C. in a vacuum oven. Following an overnight prehybridization at 65° C., the nitrocellulose filter was hybridized overnight at 65° C. with a cDNA insert of phage 519.11 (5×10$^6$ cpm/ml), labeled with

```
                20                         40                         60
CCTGGGCCCTCCTGCTCCTTGCAGCCATGCTCCTGGGCAACCCAGCCCCTGCCTCCGCAT
                80                        100                        120
CTGCGTGGTGAAGGCCATTGGCCTCATCGGTGGATCTGCGTTTCCTCGGGCCCACACTGT
               140                        160                        180
CTAGGATTGTGCGGGGCTGGTGAGAGAACAAGATCTCTTCCGTGTTCAAGGCAGACTTCC
               200                        220                        240
TGCCCCCTGCACCCTGCTCTCTCCCGGGCCTTGAGGTCAGTGTGAGCCCCAAGGGCAAGA
               260                        280                        300
ACACTTCTGGAAGGGAGAGTGGATTTGGCTGGGCCTCTGGATGGAAGGTCTGGTCTTCTC
                                                Met Glu Gly Leu Val Phe Se
               320                        340                        360
TCGTCTGAGCCCTGAGTACTACGACCCGGCAAGAGCCCACCTGCGTGATGGGGAGAAATC
r Arg Leu Ser Pro Glu Tyr Tyr Asp Pro Ala Arg Ala His Leu Arg Asp Gly Glu Lys Se
                  10                         20
               380                        400                        420
CTGCCCGTGCGGGCAGGAGGGCCCCCAGGGTGACCTGTTGACCAAAACACAGGAGCTGGG
r Cys Pro Cys Gly Gln Glu Gly Pro Gln Gly Asp Leu Leu Thr Lys Thr Gln Glu Leu Gl
                  30                         40
               440                        460                        480
CCGTGACTACAGGACCTGTCTGACGATAGTCCAAAAACTGAAGAAGATGGTGGATAAGCC
y Arg Asp Tyr Arg Thr Cys Leu Thr Ile  Val Gln Lys Leu Lys Lys Met Val Asp Lys Pr
                  50                         60
               500                        520                        540
CACCCAGAGAAGTGTTTCCAATGCTGCGACCCGGGTGTGTAGGACGGGGAGGTCACGATG
o Thr Gln Arg Ser Val Ser Asn Ala Ala Thr Arg Val Cys Arg Thr Gly Arg Ser Arg Tr
                  70                         80
               560                        580                        600
GCGCGACGTCTGCAGAAATTTCATGAGGAGGTATCAGTCTAGAGTTATCCAAGGCCTCGT
p Arg Asp Val Cys Arg Asn Phe Met Arg Arg Tyr Gln Ser Arg Val Ile  Gln Gly Leu Va
                  90                        100
               620                        640                        660
GGCCGGAGAAACTGCCCAGCAGATCTGTGAGGACCTCAGGTTGTGTATACCTTCTACAGG
l Ala Gly Glu Thr Ala Gln Gln Ile Cys Glu Asp Leu Arg Leu Cys Ile Pro Ser Thr Gl
                 110                        120
               680                        700                        720
TCCCCTCTGAGCCCTCTCACCTTGTCCTGTGGAAGAAGCACAGGCTCCTGTCCTCAGATC
y Pro Leu End
               740                        760                        780
CCGGGAACGTCAGCAACCTCTGCCGGCTCCTCGCTTCCTCGATCCAGAATCCACTCTCCA
               800                        820                        840
GTCTCCCTCCCCTGACTCCCTCTGCTGTCCTCCCCTCTCAGGGGAATAAAGTGTCAAGCA
               860                        880
AGATTTTAGCCGCAAAAAAAAAAAAAAAAAAAAAAAAAAAAAAAAAA
```

$^{32}$P using the random hexamer priming method (Feinberg and Vogelstein. *Anal. Biochem.* (1983) 132:6).

RESULTS

Isolation of Specific cDNA Clones from a Subtracted Library

To isolate cDNA clones representing genes expressed specifically in functional T-cell lines, the AH2-LB, T-B subtracted cDNA library was screened with a highly radioactive subtracted cDNA probe (T*-B cDNA probe, spec. activity $10^8$ cpm/µg) prepared from RNA extracted from the cytolytic T-cell AH-2. The cDNA was subtracted with RNA from the EBV transformed B-cell line LB. After two rounds of screening, 53 positive colonies were identified. To eliminate those clones representing rare abundance messenger RNA sequences expressed in T- and B-cells as well as other clones which were not efficiently removed by the subtraction procedure, a subtracted B*-B cDNA probe was prepared. cDNA prepared from LB cells which were subtracted under standard conditions with its template RNA was used. 17 clones were eliminated which hybridized to this B*-B probe. Finally eight clones with inserts >300 bps were selected, seven of which cross hybridized. The clone with the longest insert in this group of seven (designated AH2-519), 382 bps including 34 A residues at its 3' end, was selected for further study.

Cell Type Specific Expression of 519 RNA

The cDNA insert of clone AH2-519 was used as a probe on Northern blots containing RNA from a variety of leukemic or virally transformed cell lines of different cell lineages and several independently functional T-cell lines. 519 messenger RNA expression was detected only in functional T-cell lines, including five cytolytic T-cell lines AI5.1, AI1.1, AJY, CCD, and AH2. The expression of gene 519 is not restricted to functional cytolytic T-cells since the five functional helper T-cell lines, AJ13.1, AJ8.1, APL2, APL1 and APL2, contain 519 messenger RNA at levels comparable to the functional cytolytic T-cell lines. The 519 messenger RNA is detected as a diffuse band with an average length of approximately 900 nt. The diffuse appearance of the 519 specific RNA may be due to incomplete denaturation under the conditions used for sample preparation prior to loading the gel. Shorter exposures of the autoradiogram do not reveal evidence for the presence of more than one size of messenger RNA. As expected, 519 messenger RNA was not detected in five EBV transformed B-cell lines (TOTO, PALLY, LCL-721, DAUDI and LB). In addition, three non-lymphoid tumor lines, the promyelocytic leukemia line HL60, the myelomonocytic leukemia line U937, and the erythroleukemia line K562, are negative for 519 expression as well. 519 RNA expression was not found in six established T-cell tumor lines (MOLT3, HUT78, HSB, HPB-ALL, Jurkat and MOLT4). Thus, among the in vitro derived tissue culture cells tested, the expression of 519 RNA is restricted to non-transformed, functional T-cell lines.

To investigate whether other non-transformed cells express 519 RNA, a Northern blot containing RNA from a variety of normal tissues was hybridized. None of the tissues tested (tonsil, placenta, lung, liver, skeletal and smooth muscle) express 519 RNA. In addition, a human fibroblast cell line KB is also negative.

These results show that the expression of the 519 gene is not a characteristic of all non-transformed cells, but is restricted to IL-2 dependent, antigen driven functional T-cell lines.

The Inducible Expression of 519 RNA

The restricted expression pattern of 519 RNA suggests that the expression of the 519 gene is regulated by the periodic addition of IL-2 and antigen to the functional T-cell lines. 519 mRNA expression was measured is cultures of normal PBL, stimulated for different periods of time with antigen in a mixed lymphocyte reaction or stimulated with the mitogen phytohemagglutinin (PHA). Both kinds of stimulation lead to the early synthesis and release of IL-2. Freshly derived PBL express 519 RNA. No change in expression of 519 RNA is detected in PBL grown for one day or three days in a mixed lymphocyte culture or in the presence of PHA. However, in both types of cultures a dramatic increase in the expression of 519 RNA can be detected five days after the start of the culture. Cultures tested at day seven do not reveal a further increase in 519 RNA expression. Further time points were not tested.

To determine whether the expression of 519 RNA is inducible in other activated lymphocytes, splenic B-cells were activated with fixed *Staphylococcus aureus*. After three days, at the time of maximum blast formation, the cells were harvested and depleted of activated T-cells by treatment with anti-CD2 and anti-CD3 monoclonal antisera and complement. RNA extracted from the treated cells did not hybridize with 519 probe.

Thus, these experiments show that the expression of the 519 gene is regulated in normal T-cells, but not in normal B-cells, by mitogenic or antigenic stimulation.

Isolation and Sequence Analysis of a Full-Length 519 Clone

Using the short AH2-519 clone as a probe, a λgt10 cDNA library prepared from total cytoplasmic polyA+ RNA from AH2 cells was screened. One clone, 519.11, was selected because the length of its insert is similar to the size of the 519 specific messenger RNA as determined by Northern analysis. The DNA sequences of both the short AH2-519 and the longer 519.11 clones were determined. The two clones overlap from bp 504-bp 810. The sequence from both clones permitted deduction of the sequence of the 519 messenger RNA to be minimally 853 nucleotides, exclusive of the polyA tail and possibly some nucleotides at the 5' end not included in the 519.11 clone. The DNA sequence as derived from these two overlapping clones is shown above.

Inspection of this sequence revealed the following: 1) comparison of the DNA sequence or the predicted amino acid sequence revealed no homology with published sequences compiled in the GenBank and NBRF databases. 2) There is a single long open reading frame coding for a protein of 129 amino acids with a predicted $M_r$ of 14,600, starting at the ATG codon at position 281 and terminating at the TGA codon at position 668. The presumed initiation ATG codon is the second ATG in the sequence. The first ATG at position 27 is followed by an in frame stop codon at position 69. It is noteworthy that the ATG sequence at position 281 has little homology to the Kozak consensus sequence for eukaryotic translation initiation sites (TGGATGG versus the consensus ACCATGG, Kozak, *Nucl. Acids Res.* (1984) 12:857). 3) A single polyadenylation signal is present at position 825 (AATAAA) followed by a stretch of 34 A residues starting at position 853. 4) A hydropathy plot from the predicted amino acid sequence shows that the predicted protein is very hydrophilic and although it contains some hydrophobic regions, no region long enough to constitute a membrane spanning domain appears to be present. The amino acid sequence of the N-terminal part of the predicted protein does not resemble the typical sequence found in eukaryotic signal peptides. Taken together, this suggests that the 519 gene product is not a membrane bound or secreted protein. 5) The overall charge of the protein is likely to be positive since it contains more basic than acidic residues (22 Arg and Lys residues versus 14 Glu and Asp residues). 6) No potential N-linked glycosylation sites are present in the predicted sequence.

In Vitro Transcription and Translation of 519.11

To unequivocally determine the coding strand and the translational capacity of clone 519.11, the 519.11 insert was subcloned into the vector pGem-1 and both strands were transcribed using either SP6 or T7 polymerase (Krieg and Melton, *Nucl. Acids Res.* (1984) 12:7057). Both RNA preparations were then translated in vitro in a rabbit reticulocyte extract. The sense RNA containing the polyA tract at its 3' end is translated into a protein with an $M_r$ of approximately 15,000, in close agreement with the predicted $M_r$ of 14,600. No specific translation products are detectable using the antisense RNA strand as a template in the rabbit reticulocyte extract. The in vitro generated RNA is inefficiently translated compared with either the globin RNA or the BMV RNA supplied as positive control RNA's with the reticulocyte extract. Mixing experiments suggest that this is not due to impurities in the 519 RNA preparation. The poor translational efficiency may be related to the presence of the short open reading frame which can potentially code for a 14 amino acid long peptide preceding the long reading frame and/or to the poor match of the sequence surrounding the ATG codon at position 281 with the consensus sequence for eukaryotic translation initiation sites.

Southern Analysis of Genomic DNA

The $^{32}P$ labeled 519.11 fragment was hybridized with Southern blots containing genomic DNA. The DNA samples were prepared from germ line cells (sperm) or from functional CTL or EBV transformed cell lines established from peripheral blood lymphycytes (PBL) of two individuals or from the tumor line HUT78 and digested with EcoRI or BamHI or HindIII. The results with EcoRI and BamHI showed only two 519 related bands. The HindIII digest showed three 519 related bands. No differences were detected among the DNA samples extracted from different cell types of the different individuals or from the HUT78 tumor. The 519 gene is probably present in, at most, two copies per haploid genome. The absence of 519 RNA expression in B-lymphoblasts or T-cell tumor lines is not due to gross rearrangement or loss of the 519 gene.

It is evident from the above results, that the subject invention provides peptides and nucleic acids which find use in diagnosis for the status of a particular cell. In particular, the presence of the RNA or peptide is indicative of stimulation of a functional T-cell which is not neoplastic. Furthermore, the level of the subject peptide is indicative of the period of time which has transpired since stimulation, low levels indicating either recent stimulation or an extended period having transpired since stimulation, while high levels indicating stimulation having occurred in the recent past.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for determining whether a T-cell is stimulated or unstimulated comprising:
    determining the level of transcription or translation of messenger RNA encoding the peptide 519, wherein an increase in the level of transcription or translation of messenger RNA encoding peptide 519 compared to the level of transcription or translation of messenger RNA encoding peptide 519 in an unstimulated T-cell indicates a stimulated T-cell.

* * * * *